United States Patent
Bevins, III et al.

(10) Patent No.: US 7,195,685 B2
(45) Date of Patent: Mar. 27, 2007

(54) NONWOVEN FABRIC HAVING IMPROVED PERFORMANCE

(75) Inventors: Errette Bevins, III, Mountain Top, PA (US); Nick Carter, Mooresville, NC (US); Sergio Diaz de Leon, Clayton, NC (US)

(73) Assignee: Polymer Group, Inc., Charlotte, NC (US)

( * ) Notice: Subject to any disclaimer, the term of this patent is extended or adjusted under 35 U.S.C. 154(b) by 0 days.

(21) Appl. No.: 10/797,400

(22) Filed: Mar. 10, 2004
(Under 37 CFR 1.47)

(65) Prior Publication Data
US 2005/0039837 A1    Feb. 24, 2005

Related U.S. Application Data

(60) Provisional application No. 60/453,410, filed on Mar. 10, 2003.

(51) Int. Cl.
    *B32B 31/30*    (2006.01)
    *B32B 27/02*    (2006.01)
    *B32B 27/32*    (2006.01)

(52) U.S. Cl. .................. 156/167; 156/179; 156/181; 264/113

(58) Field of Classification Search ............ None
See application file for complete search history.

(56) References Cited

U.S. PATENT DOCUMENTS

| 3,260,778 | A |   | 7/1966  | Walton             |         |
|-----------|---|---|---------|--------------------|---------|
| 3,416,194 | A |   | 12/1968 | Packard            |         |
| 3,810,280 | A |   | 5/1974  | Walton et al.      |         |
| 3,837,995 | A | * | 9/1974  | Flooden            | 442/345 |
| 4,029,101 | A |   | 6/1977  | Chesky et al.      |         |
| 4,041,203 | A | * | 8/1977  | Brock et al.       | 428/157 |
| 4,082,878 | A | * | 4/1978  | Boe et al.         | 428/195.1 |
| 4,090,385 | A |   | 5/1978  | Packard            |         |
| 4,184,498 | A |   | 1/1980  | Franco             |         |
| 4,195,634 | A |   | 4/1980  | DiSalvo et al.     |         |
| 4,408,357 | A |   | 10/1983 | Toth               |         |
| 4,573,986 | A |   | 3/1986  | Minetola et al.    |         |
| 4,717,329 | A |   | 1/1988  | Packard et al.     |         |
| 4,784,892 | A | * | 11/1988 | Storey et al.      | 428/172 |
| 4,845,779 | A |   | 7/1989  | Wheeler et al.     |         |
| 4,876,746 | A |   | 10/1989 | Howie              |         |
| 4,886,513 | A |   | 12/1989 | Mason, Jr. et al.  |         |
| 5,288,544 | A | * | 2/1994  | Mallen et al.      | 442/198 |
| 5,616,408 | A |   | 4/1997  | Oleszczuk et al.   |         |
| 5,655,374 | A |   | 8/1997  | Santilli et al.    |         |
| 5,678,379 | A |   | 10/1997 | Quattrociocchi     |         |
| 5,766,737 | A |   | 6/1998  | Willey et al.      |         |
| 5,843,056 | A |   | 12/1998 | Good et al.        |         |
| 5,951,535 | A | * | 9/1999  | Fujiwara et al.    | 604/384 |
| 6,029,274 | A |   | 2/2000  | Welchel et al.     |         |
| 6,103,647 | A |   | 8/2000  | Shultz et al.      |         |

(Continued)

*Primary Examiner*—Sam Chuan Yao
(74) *Attorney, Agent, or Firm*—Kilyk & Bowersox, P.L.L.C.; Valerie Calloway

(57) ABSTRACT

The present invention relates generally to nonwoven materials, and specifically, to a nonwoven fabric comprised of at least three continuous filament precursor webs, each precursor web being of a thermoplastic polymer dissimilar from the other precursor webs, wherein the resulting durable nonwoven laminate fabric exhibits improved tactile and ductile qualities, as well as improved tensile strength, the nonwoven fabric being eminently suitable for application in improving the comfort and use of hygiene, medical and industrial products.

13 Claims, 1 Drawing Sheet

U.S. PATENT DOCUMENTS

| | | |
|---|---|---|
| 6,144,017 A | 11/2000 | Fabbricante et al. |
| 6,191,211 B1 | 2/2001 | Mussell et al. |
| 6,198,018 B1 | 3/2001 | Curro |
| 6,264,864 B1 | 7/2001 | Mackay |
| 6,290,979 B1 | 9/2001 | Roe et al. |
| 6,340,413 B1 | 1/2002 | Nilsson et al. |
| 2002/0148547 A1* | 10/2002 | Abed et al. ................ 156/62.2 |

* cited by examiner

NONWOVEN FABRIC HAVING IMPROVED PERFORMANCE

TECHNICAL FIELD

This application claims benefit of a provisional application 60/453,410 filed on Mar. 10, 2003.

The present invention relates generally to nonwoven materials, and specifically, to a nonwoven fabric comprised of at least three continuous filament precursor webs formed from a juxtaposition of a first outer layer comprising a thermoplastic precursor web of continuous filaments, a second outer layer thermoplastic precursor web, also of continuous filaments, and a central thermoplastic precursor web of continuous filaments positioned between the first and second outer layer, each precursor web being of a thermoplastic polymer dissimilar from at least one of the other precursor webs, wherein the resulting nonwoven laminate fabric exhibits improved tactile and ductile qualities, as well as strength, the nonwoven fabric being immanently suitable for application in improving the comfort and use of hygiene, medical and industrial products.

BACKGROUND OF THE INVENTION

Nonwoven fabrics are used in a wide variety of applications where the engineered qualities of the fabrics can be advantageously employed. The use of selected thermoplastic polymers in the construction of the fibrous fabric component, selected treatment of the fibrous component (either while in fibrous form or in an integrated structure), and selected use of various mechanisms by which the fibrous component is integrated into a useful fabric, are typical variables by which to adjust and alter the performance of the resultant nonwoven fabric.

Disposable hygiene products and personal protective apparel readily employ nonwoven fabrics in their respective constructions. Such nonwoven fabrics come in to intimate contact with the human skin for prolonged periods of time. The comfort of the product is subsequently directly attributed to the way in which the product touches the skin, the weight of the product as it is worn, and the ability of the product to conform and adapt to changes in user position. In acknowledgment of the importance of the product/human interface, conventional nonwoven fabric manufactures have gone to great efforts to improved the tactile and ductile performance of their fabrics.

Two general approaches to improving the comfort of a nonwoven fabric include chemical and mechanical alteration. Representative prior art to the use of chemical alteration of the nonwoven fabric are: U.S. Pat. No. 6,290,979, to Roe et al., teaches to the use of a first and a second skin care composition to affect the comfort of a disposable diaper; and Applicant's co-pending application, directed to the use of a two-part fatty acid amide melt additive, involves the introduction of the melt additive into the nonwoven fabric during manufacture. Mechanical alteration has been presented in the prior art in such forms as compressive technologies (MICREXING is described in U.S. Pat. Nos. 3,260,778, 3,416,192, 3,810,280, 4,090,385; and 4,717,329) and alternate nonwoven fabric formation technologies (as typified by U.S. Pat. No. 6,340,413 to Nilsson, et al.).

U.S. Pat. No. 5,766,737, to Willey et al., directed to a multilayered barrier fabric, teaches a nonwoven fabric having differential aesthetic properties obtained by the necessary incorporation of barrier meltblown layer. Such a laminate as taught by Willey et al., includes a significant quantity of meltblown material, and overall laminate basis weight, so as to render the material suitable for independent use in medical applications.

There remains an unmet need for a soft, strong, and durable nonwoven fabric, which can be used in improving the comfort of hygiene, medical and industrial products, which does not necessarily involve the use of additional additives or complex manufacturing procedures, nor adversely affects the performance of the construct or product to which it is adjoined.

SUMMARY OF THE INVENTION

The present invention relates generally to nonwoven materials, and specifically, to a nonwoven fabric comprised of at least three continuous filament precursor webs, each precursor web being of a thermoplastic polymer dissimilar from the other precursor webs, wherein the resulting durable nonwoven laminate fabric exhibits improved tactile and-ductile qualities, as well as improved tensile strength, the nonwoven fabric being eminently suitable for application in improving the comfort and use of hygiene, medical and industrial products. The nonwoven fabric is manufactured with a minimum level of process complexity, and can be either used as an absorbent article component, such as a liner for feminine hygiene products, as well as a topsheet or backsheet, when laminated with a film. The fabric is also suitable for surgical face mask material, wherein the fabric provides durability, in addition to comfort.

In a first embodiment, the nonwoven fabrics made in accordance with the present invention are formed from a juxtaposition of a first outer layer comprising a thermoplastic precursor web of continuous filaments, a second outer layer thermoplastic precursor web, also of continuous filaments, and a central thermoplastic precursor web of continuous filaments positioned between the first and second outer layers. Optionally, the continuous filament layers may be directly extruded onto one another in an in-line process. It is also within the purview of the invention to incorporate additional continuous filament layers into the nonwoven laminate.

In a second embodiment, the nonwoven fabrics made in accordance with the present invention are formed from extruding more than one type of thermoplastic continuous filament from the same spinneret, so as to incorporate more than one type of thermoplastic filament within the same precursor web. The resultant continuous filament precursor web may comprise a first thermoplastic forming a first filamentary zone and a dissimilar second thermoplastic forming a second filamentary zone. Further, the entire precursor web may comprise an even distribution of more than one thermoplastic continuous filament throughout the length and width of the web. Subsequently, the precursor webs may be positioned according the process mentioned above.

The thermoplastic polymers of the continuous filament precursor webs are chosen from the group consisting of polyesters, polyamides, nylons, polyolefins, such as polypropylene, polyethylene, and the derivatives and/or the combinations thereof. Further, the first and second outer layer precursor webs of the laminate are respectively comprised of dissimilar homogeneous filaments, as well as, performance and/or aesthetic modifying additive.

It is within the purview of the present invention that the formed fabric includes one or more centrally located layers comprised of Ziegler-Natta or Metalocene based polymers, thermally compatible thermoplastic random copolymers, performance modifying agents, and the combinations thereof, which allows for the adjoining of the two dissimilar thermoplastic outer layer precursor webs. The resulting nonwoven laminate is one that has improved tactile and ductile qualities, as well as improved strength, so as to enhance the comfort and provide durability to suitable hygiene, medical, and industrial applications end-use articles.

Other features and advantages of the present invention will become readily apparent from the following detailed description, the accompanying drawings, and the appended claims.

DETAILED DESCRIPTION

Figure 1:
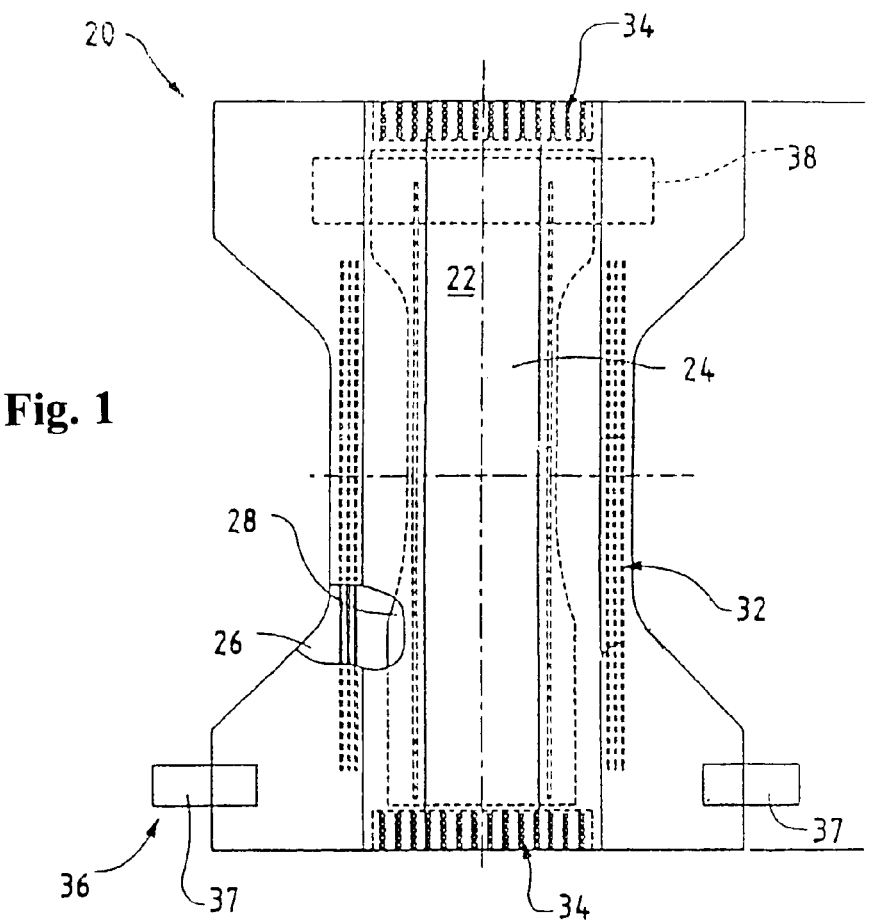
FIG. 1 is a plan view of a diaper in an uncontracted state.

While the present invention is susceptible of embodiment in various forms, there will hereinafter be described, presently preferred embodiments, with the understanding that the present disclosure is to be considered as an exemplification of the invention, and is not intended to limit the invention to the specific embodiments disclosed herein.

The present invention is directed to a strong, but soft nonwoven laminate, which entails formation of a first outer layer of thermoplastic continuous filaments, preferably of polyethylene, a second outer layer of thermoplastic continuous filaments, preferably of polypropylene, and at least one centrally located thermoplastic polymer optionally comprised of a random copolymer, wherein the central layer is preferably polypropylene or a polypropylene blend.

In general, the formation of continuous filament precursor webs involves the practice of the "spunbond" process. A spunbond process involves supplying a molten polymer, which is then extruded under pressure through a large number of orifices in a plate known as a spinneret or die. The resulting continuous filaments are quenched and drawn by any of a number of methods, such as slot draw systems, attenuator guns, or Godet rolls. The continuous filaments are collected as a loose web upon a moving foraminous surface, such as a wire mesh conveyor belt. When more than one spinneret is used in line for the purpose of forming a multi-layered fabric, the subsequent webs are collected upon the uppermost surface of the previously formed web.

It is within the purview of the present invention that at least one of the continuous filament precursor webs may be formed from filaments having a nano-denier, as taught in U.S. Pat. Nos. 5,678,379 and 6,114,017, both incorporated herein by reference. Further, at least one of the continuous filament precursor webs may be formed from an intermingling of conventional and nano-denier filaments.

In addition to the aforementioned conventional spunbond practice, the precursor webs of the present invention may be formed by extruding more than one thermoplastic, such as polypropylene, polyethylene, a random copolymer blend of polypropylene or polyethylene, or a combination thereof, from the same spinneret. Formation of the precursor web in this manner may provide for a web with two or more filamentary zones, wherein one half of the web may be formed of polypropylene filaments and the other half formed of polyethylene filaments. Further, the web may be comprised of alternating zones or the entire web may comprise an equal distribution of polypropylene and polyethylene filaments.

The meltblown process is a related means to the spunbond process for forming a layer of a nonwoven fabric is the meltblown process. It has been contemplated that additional layers be added located centrally to the first and second outer layer, wherein one or more of centrally located layers may be a meltblown layer. Again, a molten polymer is extruded under pressure through orifices in a spinneret or die. High velocity air impinges upon and entrains the filaments as they exit the die. The energy of this step is such that the formed filaments are greatly reduced in diameter and are fractured so that microfibers of finite length are produced. This differs from the spunbond process whereby the continuity of the filaments is preserved. The process to form either a single layer or a multiple-layer fabric is continuous, that is, the process steps are uninterrupted from extrusion of the filaments to form the first layer until the bonded web is wound into a roll. Methods for producing these types of fabrics are described in U.S. Pat. No. 4,041,203. The meltblown process, as well as the cross-sectional profile of the meltblown microfiber, is not a critical limitation to the practice of the present invention.

The laminate comprising a first and second outer thermoplastic precursor web of dissimilar composition, and a centrally located thermoplastic layer, are then consolidated, usually by means involving heat and pressure, such as by thermal point or ultrasonic bonding. Using this means, the web or layers of webs are passed between two hot metal rolls, one of which has an embossed pattern to impart and achieve the desired degree of point bonding, usually on the order of 10 to 40 percent of the overall surface area being so bonded.

The centrally located continuous filament layer acts as a bonding agent so as to assist in the consolidation process. It is in the purview of the present invention that the central layer be comprised of either a Ziegler-Natta or Metalocene based thermoplastic polymer, such as a high melt flow, low melt temperature polypropylene, a random copolymer, a performance modifying agent, such as a tackifier, and the combinations thereof.

Manufacture of nonwoven compound fabrics embodying the principles of the present invention includes the use of thermoplastic filaments having different composition. Differing thermoplastic polymers, include, but are not limited to polyesters, polyamides, nylons, polyolefins, and the combinations thereof, which can be further compounded with the same or different performance improvement additives. Further still, filaments that have been treated with performance improvement additives may be blended with filaments that have not been modified by the compounding of additives.

In accordance with the present invention, the continuous filament laminate construct may comprise an additional film layer. The formation of finite thickness films from thermoplastic polymers, suitable as a strong and durable carrier substrate layer, is a well-known practice. Thermoplastic polymer films can be formed by either dispersion of a quantity of molten polymer into a mold having the dimensions of the desired end product, known as a cast film, or by continuously forcing the molten polymer through a die, known as an extruded film. Extruded thermoplastic polymer films can either be formed such that the film is cooled then wound as a completed material, or dispensed directly onto a secondary substrate material to form a composite material having performance of both the substrate and the film layers.

Extruded films can be formed in accordance with the following representative direct extrusion film process. Blending and dosing storage comprising at least one hopper loader for thermoplastic polymer chip and, optionally, one for pelletized additive in thermoplastic carrier resin, feed into variable speed augers. The variable speed augers transfer predetermined amounts of polymer chip and additive pellet into a mixing hopper. The mixing hopper contains a mixing propeller to further the homogeneity of the mixture. Basic volumetric systems such as that described are a minimum requirement for accurately blending the additive into the thermoplastic polymer. The polymer chip and additive pellet blend feeds into a multi-zone extruder. Upon mixing and extrusion from the multi-zone extruder, the polymer compound is conveyed via heated polymer piping through a screen changer, wherein breaker plates having different screen meshes are employed to retain solid or semi-molten polymer chips and other macroscopic debris. The mixed polymer is then fed into a melt pump, and then to a combining block. The combining block allows for multiple film layers to be extruded, the film layers being of either the same composition or fed from different systems as described above. The combining block is connected to an extrusion die, which is positioned in an overhead orientation such that molten film extrusion is deposited at a nip between a nip roll and a cast roll.

In addition, breathable films can be used in conjunction with the disclosed continuous filament laminate. Monolithic films, as taught in U.S. Pat. No. 6,191,211, and microporous films, as taught in U.S. Pat. No. 6,264,864, both patents herein incorporated by reference, represent the mechanisms of forming such breathable films.

A number of end-use articles can benefit from the inclusion of the soft, yet durable laminate of the present invention, including, but not limited to, hygiene absorbent articles, such as diapers and catamenial products, hygienic wipes, and medical/industrial protective articles.

Disposable waste-containment garments are generally described in U.S. Pat. Nos. 4,573,986, 5,843,056, and 6,198,018, which are incorporated herein by reference.

An absorbent article incorporating an improved lightweight facing fabric of the present invention is represented by the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinence briefs, incontinence undergarments, diaper holders and liners, feminine hygiene garments, training pants, pull-on garments, and the like.

FIG. 1 is a plan view of a diaper 20 in an uncontracted state (i.e., with elastic induced contraction pulled out) with portions of the structure being cut-away to more clearly show the construction of the diaper 20. As shown in FIG. 1, the diaper 20 preferably comprises a containment assembly 22 comprising a liquid pervious topsheet 24; a liquid impervious backsheet 26 joined to the topsheet; and an absorbent core 28 positioned between the topsheet 24 and the backsheet 26. The absorbent core 28 has a pair of opposing longitudinal edges, an inner surface and an outer surface. The diaper can further comprise elastic leg features 32; elastic waist features 34; and a fastening system 36, which preferably comprises a pair of securement members 37 and a landing member 38.

Catamenial products, such as feminine hygiene pads, are of the same general construction as the aforementioned diaper structure. Again, a topsheet and a backsheet are affixed about a central absorbent core. The overall design of the catamenial product is altered to best conform to the human shape and for absorbing human exudates. Representative prior art to such article fabrication include U.S. Pat. Nos. 4,029,101, 4,184,498, 4,195,634, 4,408,357 and 4,886,513, which are together incorporated herein by reference.

Medical and industrial protective products, such as CSR, medical gown, surgical drape, medical wipes, face masks, and oversuits can benefit significantly from the inclusion of a soft and durable fabric as described in the present invention. Of particular utility in the fabrication of such protective products is the use of lighter weight and improved comfort fabrics that will allow for finished product to still perform the desired function. Patents generally describing such protective products include U.S. Pat. Nos. 4,845,779, 4,876,746, 5,655,374, 6,029,274, and 6,103,647, which are together incorporated herein by reference.

Figure 2:
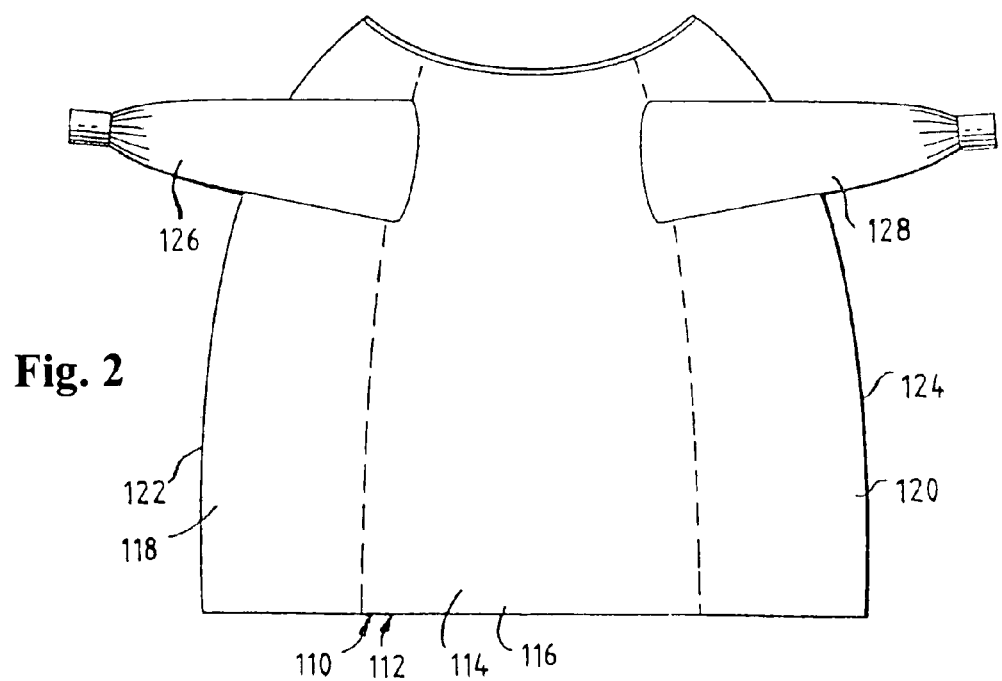
FIG. 2 is a plan view of a surgical gown.

Referring now to FIG. 2, there is shown a disposable garment generally designated 110 comprising a surgical gown 112. The gown 112 comprises a body portion 114, which may be one-piece, having a front panel 116 for covering the front of the wearer, and a pair of back panels 118 and 120 extending from opposed sides of the front panel 116 for covering the back of the wearer. The back panels 118 and 120 have a pair of side edges 122 and 124, respectively, which define an opening on the back of the gown. The gown 112 has a pair of sleeves 126 and 128 secured to the body portion 114 of the gown for the arms of the wearer. In use, the back panels 118 and 120 overlap on the back of the wearer in order to close the back opening of the gown, and suitable belt means (not shown) is utilized to secure the back panels 118 and 120 in the overlapping relationship.

From the foregoing, numerous modifications and variations can be effected without departing from the true spirit and scope of the novel concept of the present invention. It is to be understood that no limitation with respect to the specific embodiments disclosed herein is intended or should be inferred. The disclosure is intended to cover, by the appended claims, all such modifications as fall within the scope of the claims.

What is claimed is:

1. A method for forming a soft, durable nonwoven laminate fabric comprising the steps of:
   a. providing a first thermoplastic polymer,
   b. providing a second thermoplastic polymer, wherein said second thermoplastic polymer is dissimilar to said first thermoplastic polymer,
   c. providing a third thermoplastic polymer, wherein said third thermoplastic polymer is dissimilar to said first thermoplastic polymer,
   d. forming said first thermoplastic polymer into a first continuous filament precursor web,
   e. forming said second thermoplastic polymer into a second continuous filament precursor web,
   f. forming said third thermoplastic polymer into a third continuous filament precursor web, wherein all fabric material of the third continuous filament precursor web consists of thermoplastic filaments, wherein said third continuous filament precursor web is positioned between said first and second continuous filament precursor webs, and
   g. consolidating said first, second, and third continuous filament precursor webs by application of elevated temperature and pressure to form a nonwoven laminate fabric, wherein said third continuous filament precursor web alone acts as a bonding agent for said consolidating step.

2. A method for forming a soft, durable nonwoven laminate fabric as in claim 1, wherein said first thermoplastic polymer is polyethylene.

3. A method for forming a soft, durable nonwoven laminate fabric as in claim 1, wherein said second thermoplastic polymer is polypropylene.

4. A method for forming a soft, durable nonwoven laminate fabric as in claim 1, wherein said third thermoplastic polymer is a polypropylene blend.

5. A method for forming a soft, durable nonwoven laminate fabric as in claim 1, wherein said consolidation of said first, second, and third precursor webs is a calendaring process, wherein said calendaring process comprises a heated embossed roll and a heated smooth roll; wherein said heated embossed roll is of a higher temperature than said heated smooth roll.

6. A method for forming a soft, durable nonwoven laminate fabric as in claim 5, wherein said first precursor web comprises polyethylene and is in direct contact with said smooth roll.

7. A method for forming a soft, durable nonwoven laminate fabric as in claim 5, wherein said consolidation comprises bonding 10 to 40 percent of overall surface area of the first, second, and third continuous filament precursor webs.

8. A method for forming a soft, durable nonwoven laminate fabric as in claim 1, wherein said third continuous filament precursor web is comprised of a fiber material selected from the group consisting of a Ziegler-Natta-based thermoplastic polymer, metallocene-based thermoplastic polymer, a random copolymer, and a tackifier-containing polymer composition.

9. A method for forming a soft, durable nonwoven laminate fabric as in claim 1, wherein the thermoplastic polymer of the third continuous filament precursor web is selected from the group consisting of polyesters, polyamides, nylons, polyolefins, and/or combinations thereof.

10. A method for forming a soft, durable nonwoven laminate fabric comprising the steps of:
   a. providing a first thermoplastic polymer,
   b. providing a second thermoplastic polymer, wherein said second thermoplastic polymer is dissimilar to said first thermoplastic polymer,
   c. providing a third thermoplastic polymer, wherein said third thermoplastic polymer is dissimilar to said first thermoplastic polymer,
   d. forming said first thermoplastic polymer into a first continuous filament precursor web,
   e. forming said second thermoplastic polymer into a second continuous filament precursor web,
   f. forming said third thermoplastic polymer into a third continuous filament precursor web, wherein all fabric material of the third continuous filament precursor web consists of thermoplastic filaments,
   g. juxtaposing said first continuous filament precursor web in a face-to-face relationship with said third filament precursor web, and said second continuous filament precursor web in a face-to-face relationship with said third filament precursor web, and
   h. consolidating said first, second, and third continuous filament precursor webs by application of elevated temperature and pressure to form a nonwoven laminate fabric comprising tackifying said third filament precursor web alone effective to provide consolidation of said first, second, and third continuous filament precursor webs.

11. A method for forming a soft, durable nonwoven laminate fabric as in claim 10, wherein said consolidation comprises bonding 10 to 40 percent of overall surface area of the first, second, and third continuous filament precursor webs.

12. A method for forming a soft, durable nonwoven laminate fabric as in claim 10, wherein said third continuous filament precursor web is comprised of a fiber material selected from the group consisting of a Ziegler-Natta-based thermoplastic polymer, metallocene-based thermoplastic polymer, a random copolymer, and a tackifier containing polymer composition.

13. A method for forming a soft, durable nonwoven laminate fabric as in claim 10, wherein the thermoplastic polymer of the third continuous filament precursor web is selected from the group consisting of polyesters, polyamides, nylons, polyolefins, and/or combinations thereof.

* * * * *